United States Patent
Weeber

(10) Patent No.: US 8,862,447 B2
(45) Date of Patent: Oct. 14, 2014

(54) APPARATUS, SYSTEM AND METHOD FOR PREDICTIVE MODELING TO DESIGN, EVALUATE AND OPTIMIZE OPHTHALMIC LENSES

(75) Inventor: Hendrik A. Weeber, Groningen (NL)

(73) Assignee: AMO Groningen B.V., Groningen (NL)

( * ) Notice: Subject to any disclaimer, the term of this patent is extended or adjusted under 35 U.S.C. 154(b) by 521 days.

(21) Appl. No.: 12/771,550

(22) Filed: Apr. 30, 2010

(65) Prior Publication Data

US 2011/0270596 A1    Nov. 3, 2011

(51) Int. Cl.
| | | |
|---|---|---|
| G06G 7/48 | (2006.01) | |
| G02C 7/02 | (2006.01) | |
| G02C 7/04 | (2006.01) | |
| G02C 7/06 | (2006.01) | |
| A61F 2/16 | (2006.01) | |

(52) U.S. Cl.
CPC .. G02C 7/02 (2013.01); G02C 7/04 (2013.01); G02C 7/041 (2013.01); G02C 7/06 (2013.01); A61F 2/16 (2013.01)
USPC .................................................. 703/6; 703/2

(58) Field of Classification Search
CPC ............ G06F 19/3437; G02B 27/0075; G02B 5/1895; G02B 3/06
USPC ................... 703/1, 2, 11; 351/159.74, 159.21
See application file for complete search history.

(56) References Cited

U.S. PATENT DOCUMENTS

| | | |
|---|---|---|
| 2,077,092 A | 4/1937 | Broder |
| 3,305,294 A | 2/1967 | Alvarez |
| 3,367,734 A | 2/1968 | Bystricky et al. |
| 3,735,685 A | 5/1973 | Plummer |
| 4,010,496 A | 3/1977 | Neefe |
| 4,077,071 A | 3/1978 | Freeman |
| 4,093,361 A | 6/1978 | Erickson et al. |
| 4,134,160 A | 1/1979 | Bayers |

(Continued)

FOREIGN PATENT DOCUMENTS

| | | |
|---|---|---|
| DE | 8107675 U1 | 7/1981 |
| DE | 3439551 A1 | 4/1986 |

(Continued)

OTHER PUBLICATIONS

Cheng, Xu, Arthur Bradley, and Larry N. Thibos. "Predicting subjective judgment of best focus with objective image quality metrics." Journal of Vision 4.4 (2004).*

(Continued)

*Primary Examiner* — Aniss Chad
(74) *Attorney, Agent, or Firm* — AMO Groningen B.V.

(57) ABSTRACT

An apparatus, system and method for predictive modeling to design, evaluate and optimize ophthalmic lenses is disclosed. Ophthalmic lenses may include, for example, contacts, glasses or intraocular lenses (IOLs). The apparatus, system and method may include a design tool for designing a lens for implantation in an eye having a plurality of characteristics, a simulator for simulating performance of the lens in at least one modeled eye having the plurality of characteristics, at least one input for receiving clinical performance of the lens in the eye having the plurality of characteristics, a comparator for comparing outcomes of the clinical performance and the simulated performance, and an optimizer for optimizing a subsequent one of the outcome of the clinical performance responsive to modification of the lens in accordance with modification to the simulated performance.

14 Claims, 11 Drawing Sheets

(56) References Cited

U.S. PATENT DOCUMENTS

| | | | |
|---|---|---|---|
| 4,162,122 A | 7/1979 | Cohen | |
| 4,174,543 A | 11/1979 | Kelman | |
| 4,210,391 A | 7/1980 | Cohen | |
| 4,249,272 A | 2/1981 | Poler | |
| 4,254,509 A | 3/1981 | Tennant | |
| 4,254,510 A | 3/1981 | Tennant | |
| 4,316,293 A | 2/1982 | Bayers | |
| 4,319,564 A | 3/1982 | Karickhoff | |
| 4,338,005 A | 7/1982 | Cohen | |
| 4,340,283 A | 7/1982 | Cohen | |
| 4,370,760 A | 2/1983 | Kelman | |
| 4,377,873 A | 3/1983 | Reichert | |
| 4,402,579 A | 9/1983 | Poler | |
| 4,403,353 A | 9/1983 | Tennant | |
| 4,404,694 A | 9/1983 | Kelman | |
| 4,409,691 A | 10/1983 | Levy | |
| 4,424,597 A | 1/1984 | Schlegel | |
| 4,446,581 A | 5/1984 | Blake | |
| 4,480,340 A | 11/1984 | Shepard | |
| 4,500,382 A | 2/1985 | Foster | |
| 4,504,982 A | 3/1985 | Burk | |
| 4,551,864 A | 11/1985 | Akhavi | |
| 4,556,998 A | 12/1985 | Siepser | |
| 4,560,383 A | 12/1985 | Leiske | |
| 4,605,409 A | 8/1986 | Kelman | |
| 4,605,411 A | 8/1986 | Fedorov et al. | |
| 4,629,460 A | 12/1986 | Dyer | |
| 4,629,462 A | 12/1986 | Feaster | |
| 4,637,697 A | 1/1987 | Freeman | |
| 4,642,112 A | 2/1987 | Freeman | |
| 4,655,565 A | 4/1987 | Freeman | |
| 4,673,406 A | 6/1987 | Schlegel | |
| 4,676,791 A | 6/1987 | LeMaster et al. | |
| 4,676,792 A | 6/1987 | Praeger | |
| 4,681,102 A | 7/1987 | Bartell | |
| 4,687,484 A | 8/1987 | Kaplan | |
| 4,687,485 A | 8/1987 | Lim et al. | |
| RE32,525 E | 10/1987 | Pannu | |
| 4,725,277 A | 2/1988 | Bissonette | |
| 4,734,095 A | 3/1988 | Siepser | |
| 4,778,462 A | 10/1988 | Grendahl | |
| 4,781,717 A | 11/1988 | Grendahl | |
| 4,787,903 A | 11/1988 | Grendahl | |
| 4,787,904 A | 11/1988 | Severin et al. | |
| 4,795,462 A | 1/1989 | Grendahl | |
| 4,798,608 A | 1/1989 | Grendahl | |
| 4,798,609 A | 1/1989 | Grendahl | |
| 4,828,558 A | 5/1989 | Kelman | |
| 4,834,748 A | 5/1989 | McDonald | |
| 4,863,539 A | 9/1989 | Lee et al. | |
| 4,898,461 A | 2/1990 | Portney | |
| 4,932,970 A | 6/1990 | Portney | |
| 4,995,714 A | 2/1991 | Cohen | |
| 4,995,715 A | 2/1991 | Cohen | |
| 4,997,442 A | 3/1991 | Barrett | |
| 5,016,977 A | 5/1991 | Baude et al. | |
| 5,019,097 A | 5/1991 | Knight et al. | |
| 5,047,052 A | 9/1991 | Dubroff | |
| 5,054,905 A | 10/1991 | Cohen | |
| 5,056,908 A | 10/1991 | Cohen | |
| 5,066,301 A | 11/1991 | Wiley | |
| 5,071,432 A | 12/1991 | Baikoff | |
| 5,078,742 A | 1/1992 | Dahan | |
| 5,089,023 A | 2/1992 | Swanson | |
| 5,096,285 A | 3/1992 | Silberman | |
| 5,114,220 A | 5/1992 | Baude et al. | |
| 5,117,306 A | 5/1992 | Cohen | |
| 5,120,120 A | 6/1992 | Cohen | |
| 5,121,979 A | 6/1992 | Cohen | |
| 5,121,980 A | 6/1992 | Cohen | |
| 5,133,749 A | 7/1992 | Nordan | |
| 5,144,483 A | 9/1992 | Cohen | |
| 5,147,395 A | 9/1992 | Willis | |
| 5,147,397 A | 9/1992 | Christ et al. | |
| 5,184,405 A | 2/1993 | Cress | |
| 5,197,981 A | 3/1993 | Southard | |
| 5,201,763 A | 4/1993 | Brady et al. | |
| 5,203,790 A | 4/1993 | McDonald | |
| 5,217,491 A | 6/1993 | Vanderbilt | |
| 5,225,858 A | 7/1993 | Portney | |
| 5,229,797 A | 7/1993 | Futhey et al. | |
| 5,258,025 A | 11/1993 | Fedorov et al. | |
| 5,278,592 A | 1/1994 | Marie et al. | |
| 5,408,281 A | 4/1995 | Zhang | |
| 5,433,745 A | 7/1995 | Graham et al. | |
| 5,476,513 A | 12/1995 | Brady et al. | |
| 5,479,220 A | 12/1995 | Komatsu et al. | |
| 5,567,365 A | 10/1996 | Weinschenk, III et al. | |
| 5,571,177 A | 11/1996 | Deacon et al. | |
| 5,620,720 A | 4/1997 | Glick et al. | |
| 5,628,796 A | 5/1997 | Suzuki | |
| 5,652,638 A | 7/1997 | Roffman et al. | |
| 5,691,800 A | 11/1997 | Iki et al. | |
| 5,699,142 A | 12/1997 | Lee et al. | |
| 5,716,403 A | 2/1998 | Tran et al. | |
| 5,748,282 A | 5/1998 | Freeman | |
| 5,760,871 A | 6/1998 | Kosoburd et al. | |
| 5,796,462 A | 8/1998 | Roffman et al. | |
| 5,801,807 A | 9/1998 | Satake et al. | |
| 5,928,282 A | 7/1999 | Nigam | |
| 5,968,094 A | 10/1999 | Werblin et al. | |
| 6,015,435 A | 1/2000 | Valunin et al. | |
| 6,051,024 A | 4/2000 | Cumming | |
| 6,126,283 A | 10/2000 | Wen et al. | |
| 6,126,286 A | 10/2000 | Portney | |
| 6,129,759 A | 10/2000 | Chambers | |
| 6,142,625 A | 11/2000 | Sawano et al. | |
| 6,179,870 B1 | 1/2001 | Sourdille et al. | |
| 6,210,005 B1 | 4/2001 | Portney | |
| 6,235,055 B1 | 5/2001 | Chu | |
| 6,261,321 B1 | 7/2001 | Kellan | |
| 6,319,282 B1 | 11/2001 | Nishi | |
| 6,338,559 B1 | 1/2002 | Williams et al. | |
| 6,419,697 B1 | 7/2002 | Kelman | |
| 6,457,826 B1 | 10/2002 | Lett | |
| 6,464,355 B1 | 10/2002 | Gil | |
| 6,474,814 B1 | 11/2002 | Griffin | |
| 6,488,708 B2 | 12/2002 | Sarfarazi | |
| 6,491,721 B2 | 12/2002 | Freeman et al. | |
| 6,527,389 B2 | 3/2003 | Portney | |
| 6,533,416 B1 | 3/2003 | Fermigier et al. | |
| 6,536,899 B1 | 3/2003 | Fiala | |
| 6,537,317 B1 | 3/2003 | Steinert et al. | |
| 6,547,822 B1 | 4/2003 | Lang | |
| 6,554,859 B1 | 4/2003 | Lang et al. | |
| 6,557,992 B1 | 5/2003 | Dwyer et al. | |
| 6,598,606 B2 | 7/2003 | Terwee et al. | |
| 6,609,793 B2 | 8/2003 | Norrby et al. | |
| 6,705,729 B2 | 3/2004 | Piers et al. | |
| 6,802,605 B2 * | 10/2004 | Cox et al. | 351/159.21 |
| 6,808,262 B2 | 10/2004 | Chapoy et al. | |
| 6,830,332 B2 | 12/2004 | Piers et al. | |
| 6,846,326 B2 | 1/2005 | Zadno-Azizi et al. | |
| 6,851,803 B2 | 2/2005 | Wooley et al. | |
| 6,899,425 B2 * | 5/2005 | Roffman et al. | 351/159.21 |
| 6,923,539 B2 | 8/2005 | Simpson et al. | |
| 6,923,540 B2 | 8/2005 | Ye et al. | |
| 6,986,578 B2 | 1/2006 | Jones | |
| 7,036,931 B2 | 5/2006 | Lindacher et al. | |
| 7,048,760 B2 | 5/2006 | Cumming | |
| 7,061,693 B2 | 6/2006 | Zalevsky | |
| 7,073,906 B1 | 7/2006 | Portney | |
| 7,137,702 B2 | 11/2006 | Piers et al. | |
| 7,156,516 B2 | 1/2007 | Morris et al. | |
| 7,188,949 B2 | 3/2007 | Bandhauer et al. | |
| 7,287,852 B2 | 10/2007 | Fiala | |
| 7,293,873 B2 | 11/2007 | Dai et al. | |
| 7,365,917 B2 | 4/2008 | Zalevsky | |
| 7,377,640 B2 | 5/2008 | Piers et al. | |
| 7,441,894 B2 | 10/2008 | Zhang et al. | |
| 7,455,404 B2 | 11/2008 | Bandhauer et al. | |
| 7,455,407 B2 | 11/2008 | Neal et al. | |
| 7,475,986 B2 | 1/2009 | Dai et al. | |
| 7,615,073 B2 | 11/2009 | Deacon et al. | |

(56) References Cited

U.S. PATENT DOCUMENTS

| | | |
|---|---|---|
| 7,616,330 B2 | 11/2009 | Neal et al. |
| 7,794,497 B2 | 9/2010 | Brady et al. |
| 7,857,451 B2 * | 12/2010 | Thibos et al. ............... 351/246 |
| 7,871,162 B2 | 1/2011 | Weeber |
| 8,382,281 B2 | 2/2013 | Weeber |
| 8,480,228 B2 | 7/2013 | Weeber |
| 2001/0051825 A1 | 12/2001 | Peterson |
| 2002/0118337 A1 | 8/2002 | Perrott et al. |
| 2002/0173846 A1 | 11/2002 | Blake et al. |
| 2002/0196408 A1 | 12/2002 | Bhalakia et al. |
| 2002/0196412 A1 | 12/2002 | Abitbol |
| 2003/0076478 A1 | 4/2003 | Cox |
| 2003/0171808 A1 | 9/2003 | Phillips |
| 2004/0021824 A1 | 2/2004 | Ye et al. |
| 2004/0054358 A1 | 3/2004 | Cox et al. |
| 2004/0068317 A1 | 4/2004 | Knight |
| 2004/0085515 A1 | 5/2004 | Roffman et al. |
| 2004/0106992 A1 | 6/2004 | Lang et al. |
| 2004/0111153 A1 | 6/2004 | Woods et al. |
| 2004/0150789 A1 | 8/2004 | Jones |
| 2004/0156014 A1 | 8/2004 | Piers et al. |
| 2004/0167622 A1 | 8/2004 | Sunalp et al. |
| 2004/0230299 A1 | 11/2004 | Simpson et al. |
| 2005/0096226 A1 | 5/2005 | Stock et al. |
| 2005/0125056 A1 | 6/2005 | Deacon et al. |
| 2005/0128432 A1 | 6/2005 | Altmann |
| 2005/0203619 A1 | 9/2005 | Altmann |
| 2005/0251254 A1 | 11/2005 | Brady et al. |
| 2005/0267575 A1 | 12/2005 | Nguyen et al. |
| 2006/0009816 A1 | 1/2006 | Fang et al. |
| 2006/0030938 A1 | 2/2006 | Altmann |
| 2006/0034003 A1 | 2/2006 | Zalevsky |
| 2006/0055883 A1 | 3/2006 | Morris et al. |
| 2006/0066808 A1 | 3/2006 | Blum et al. |
| 2006/0068453 A1 | 3/2006 | Altieri |
| 2006/0098162 A1 | 5/2006 | Bandhauer et al. |
| 2006/0098163 A1 | 5/2006 | Bandhauer et al. |
| 2006/0109421 A1 | 5/2006 | Ye et al. |
| 2006/0116763 A1 | 6/2006 | Simpson |
| 2006/0116764 A1 | 6/2006 | Simpson |
| 2006/0116765 A1 | 6/2006 | Blake et al. |
| 2006/0176572 A1 | 8/2006 | Fiala |
| 2006/0238702 A1 | 10/2006 | Glick et al. |
| 2006/0244904 A1 | 11/2006 | Hong et al. |
| 2006/0244916 A1 * | 11/2006 | Guillon ............... 351/246 |
| 2007/0052920 A1 | 3/2007 | Stewart et al. |
| 2007/0129803 A1 | 6/2007 | Cumming et al. |
| 2007/0171362 A1 | 7/2007 | Simpson et al. |
| 2007/0182924 A1 | 8/2007 | Hong et al. |
| 2007/0268453 A1 * | 11/2007 | Hong et al. ............... 351/177 |
| 2008/0018910 A1 | 1/2008 | Neal et al. |
| 2008/0030677 A1 | 2/2008 | Simpson |
| 2008/0161913 A1 | 7/2008 | Brady et al. |
| 2008/0161914 A1 | 7/2008 | Brady et al. |
| 2008/0231809 A1 | 9/2008 | Haigis |
| 2008/0269642 A1 | 10/2008 | Deacon et al. |
| 2008/0273169 A1 | 11/2008 | Blum et al. |
| 2008/0291393 A1 | 11/2008 | Menezes |
| 2009/0012609 A1 | 1/2009 | Geraghty et al. |
| 2009/0036980 A1 | 2/2009 | Norrby et al. |
| 2009/0062911 A1 | 3/2009 | Bogaert |
| 2009/0164008 A1 | 6/2009 | Hong et al. |
| 2009/0187242 A1 | 7/2009 | Weeber et al. |
| 2009/0210054 A1 | 8/2009 | Weeber et al. |
| 2009/0234448 A1 | 9/2009 | Weeber et al. |
| 2009/0268155 A1 | 10/2009 | Weeber |
| 2009/0268158 A1 | 10/2009 | Weeber |
| 2009/0279048 A1 | 11/2009 | Hong et al. |
| 2009/0295295 A1 | 12/2009 | Shannon et al. |
| 2009/0323020 A1 | 12/2009 | Zhao et al. |
| 2010/0016961 A1 | 1/2010 | Hong et al. |
| 2010/0016965 A1 | 1/2010 | Hong et al. |
| 2010/0082017 A1 | 4/2010 | Zickler et al. |
| 2010/0130888 A1 | 5/2010 | Deacon et al. |
| 2010/0161048 A1 | 6/2010 | Schaper, Jr. |
| 2012/0140166 A1 | 6/2012 | Zhao |

FOREIGN PATENT DOCUMENTS

| | | |
|---|---|---|
| EP | 226400 A2 | 6/1987 |
| EP | 227357 A2 | 7/1987 |
| EP | 343067 A1 | 11/1989 |
| EP | 457553 A2 | 11/1991 |
| EP | 681198 A1 | 11/1995 |
| EP | 0926531 A1 | 6/1999 |
| EP | 949529 A2 | 10/1999 |
| EP | 957331 A2 | 11/1999 |
| EP | 1424049 A1 | 6/2004 |
| EP | 1310267 B1 | 1/2008 |
| EP | 1424049 B1 | 6/2009 |
| FR | 2745711 A1 | 9/1997 |
| WO | WO-8603961 A1 | 7/1986 |
| WO | WO9222264 A1 | 12/1992 |
| WO | WO9303409 A1 | 2/1993 |
| WO | WO-9507487 A1 | 3/1995 |
| WO | WO-9856315 A1 | 12/1998 |
| WO | WO0019906 A1 | 4/2000 |
| WO | WO-0111418 A1 | 2/2001 |
| WO | WO-0135868 A1 | 5/2001 |
| WO | WO-0154569 A1 | 8/2001 |
| WO | WO0163344 A1 | 8/2001 |
| WO | WO0182839 A1 | 11/2001 |
| WO | WO0189424 A1 | 11/2001 |
| WO | WO0221194 A2 | 3/2002 |
| WO | WO03009053 A1 | 1/2003 |
| WO | WO2004034129 A1 | 4/2004 |
| WO | WO2004090611 A2 | 10/2004 |
| WO | WO2004096014 A2 | 11/2004 |
| WO | WO2005019906 A1 | 3/2005 |
| WO | WO2006025726 A1 | 3/2006 |
| WO | WO-2006032263 A2 | 3/2006 |
| WO | WO2006047698 A1 | 5/2006 |
| WO | WO2006060477 A2 | 6/2006 |
| WO | WO2006060480 A2 | 6/2006 |
| WO | WO-2007067872 A2 | 6/2007 |
| WO | WO2007092948 A1 | 8/2007 |
| WO | WO2007133384 A2 | 11/2007 |
| WO | WO2008045847 A2 | 4/2008 |
| WO | WO-2008083283 A2 | 7/2008 |
| WO | WO-2009020963 A1 | 2/2009 |
| WO | WO-2009029515 A1 | 3/2009 |
| WO | WO2009076670 A1 | 6/2009 |
| WO | WO-2009137491 A1 | 11/2009 |
| WO | WO-2010009254 A1 | 1/2010 |
| WO | WO-2010009257 A1 | 1/2010 |

OTHER PUBLICATIONS

Nio, Ying-Khay, et al. "Effect of intraocular lens implantation on visual acuity, contrast sensitivity, and depth of focus." Journal of Cataract & Refractive Surgery 29.11 (2003): 2073-2081.*

Piers P. A., et al., "Theoretical comparison of aberration-correcting customized and aspheric intraocular lenses", Journal of Refractive Surgery, 2007, 23 (4), 374-384.

International Search Report and Written Opinion for Application No. PCT/IB2011/001067, mailed on Sep. 13, 2011, 13 pages.

Piers P.A., et al., "Eye Models for the Prediction of Contrast Vision in Patients with New Intraocular Lens Designs," Optics Letters, 2004, vol. 29 (7), pp. 733-735.

Terwee T., et al., "Visualization of the Retinal Image in an Eye Model With Spherical and Aspheric, Diffractive, and Refractive Multifocal Intraocular Lenses," Journal of Refractive Surgery, 2008, vol. 24 (3), pp. 223-232.

Alfonso J.F., et al., "Prospective Study of the Acri.LISA bifocal Intraocular Lens," Journal of Cataract Refractive Surgery, 2007, vol. 33 (11), pp. 1930-1935.

Canovas C., et al., "Hybrid Adaptive-Optics Visual Simulator," Optical Letters, 2010, vol. 35 (2), pp. 196-198.

Cohen, Allen L., "Practical design of a bifocal hologram contact lens or intraocular lens," Applied Optics, 1992, 31 (19), 3750-3754.

(56) References Cited

OTHER PUBLICATIONS

Diffractive Lenses for Extended Depth of Focus and Presbyopic Correction. Presentation from Wavefront Congress held on Feb. 15, 2008, Rochester, New York.
Doskolovich L.L., et al., "Special Diffractive Lenses," SPIE, 1992, vol. 1780, pp. 393-402.
International Search Report for Application No. PCT/EP2008/061235, mailed on Mar. 5, 2009, 4 pages.
International Search Report for Application No. PCT/EP2009/051783, mailed on Apr. 28, 2009, 3 pages
International Search Report for Application No. PCT/US09/042449, mailed on Nov. 5, 2009, 5 pages.
International Search Report for Application No. PCT/US2010/038167, mailed on Sep. 27, 2010, 2 pages
Liou H.L., et al., "Anatomically Accurate, Finite Model Eye for Optical Modeling," Journal of Optical Society of America, 1997, vol. 14 (8), pp. 1684-1695.
Marsack J.D., et al., "Metrics of Optical Quality Derived From Wave Aberrations Predict Visual Performance," Journal of Vision, 2004, vol. 4 (4), pp. 322-328.
Monsoriu J.A., et al., "Devil's Lenses," Optics Express, 2007, vol. 15 (21), pp. 13858-13864.
Norrby S., et al., "Model Eyes for Evaluation of Intraocular Lenses," Applied Optics, 2007, vol. 46 (26), pp. 6595-6605.
Siedlecki D., et al., "Radial Gradient index Intraocular Lens: a Theoretical Model," Journal of Modern Optics, 2008, vol. 55 (4-5), pp. 639-647.
Van Meeteren A., "Calculations on the Optical Modulation Transfer Function of the Human Eye for White Light," Optica Acta, 1974, vol. 21 (5), pp. 395-412.
Vanden Berg T.J., "Analysis of Intraocular Straylight, Especially in Relation to Age," Optometry and Vision Science, 1995, vol. 72 (2), pp. 52-59.
Villegas E.A., et al., "Correlation between Optical and Psychophy, Sical Parameters as a Function of Defocus," Optometry and Vision Science, 2002, vol. 79 (1), pp. 60-67.
International Search Report for Application No. PCT/IB2009/005590, mailed on Sep. 30, 2009, 3 pages.
International Search Report for Application No. PCT/US08/073999, mailed on Dec. 3, 2008, 3 pages.
International Search Report for Application No. PCT/US2010/061081, mailed on Apr. 6, 2011, 2 pages.
U.S. Appl. No. 12/129,155, filed Apr. 23, 2009.
U.S. Appl. No. 11/618,325, filed Dec. 29, 2006, Brady et al.
U.S. Appl. No. 11/618,411, filed Dec. 29, 2006, Brady et al.
U.S. Appl. No. 12/109,251, filed Apr. 24, 2008.
Co-pending U.S. Appl. No. 12/503,267, filed Jul. 15, 2009.
Alio J.L., et al., "Phakic Anterior Chamber Lenses for the Correction of Myopia: A 7-Year Cumulative Analysis of Complications in 263 Cases," Ophthalmology, 1999, vol. 106 (3), pp. 458-466.
Apple D.J., et al., "Anterior Chamber Lenses Part 1: Complications and Pathology and a Review of Designs," Journal of Cataract Refractive Surgery, 1987, vol. 13 (2), pp. 157-174.
Apple D.J., et al., Eds., "Intraocular Lenses: Evolution, Designs, Complications and Pathology," in: New Concepts in Intraocular Lens Implantation, Williams & Wilkins publisher, 1989, pp. 204-221.
Apple D.J., et al., Eds., "Intraocular Lenses: Evolution, Designs, Complication and Pathology, " in: New Concepts in Intraocular Lens Implantation, Williams & Wilkins publisher, 1989, pp. 21-36.
Baikoff G., et al., "Angle-fixated Anterior Chamber Phakic Intraocular Lens for Myopia 7 to—19 Diopters, " Journal of Refractive Surgery, 1998, vol. 14 (3), pp. 282-292.
Cilco Advertisement Brochure, Oct. 1982, 3 Pages.
Co-pending U.S. Appl. No. 12/771,550, filed Apr. 30, 2010.
De Almeida M.S., et al., "Different Schematic Eyes and their Accuracy to the in Vivo Eye: A Quantitative Comparison Study," Brazilian Journal of Physics, 2007, vol. 37 (2A), 10 pages.
European Search Report for Application No. EP11165087, mailed on Jul. 22, 2011, 6 pages.
European Search Report for Application No. EP89304883, mailed on Sep. 3, 1990, 1 page.
International Preliminary Report on Patentability and Written Opinion for Application No. PCT/EP2008/061235, mailed on Mar. 2, 2010, 7 pages.
International Preliminary Report on Patentability and Written Opinion for Application No. PCT/EP2009/051783, mailed on Jun. 8, 2010, 6 pages.
International Preliminary Report on Patentability and Written Opinion for Application No. PCT/IB2009/005590, mailed on Sep. 6, 2011, 11 pages.
International Preliminary Report on Patentability and Written Opinion for Application No. PCT/US09/034555, mailed on Aug. 24, 2010, 8 pages.
International Preliminary Report on Patentability and Written Opinion for Application No. PCT/US09/042449, mailed on Nov. 17, 2010, 13 pages.
International Preliminary Report on Patentability and Written Opinion for Application No. PCT/US2008/073999, mailed on Mar. 2, 2010, 9 pages.
International Preliminary Report on Patentability for Application No. PCT/US081061180, mailed on Oct. 27, 2009, 1 page.
International Preliminary Report on Patentability for Application No. PCT/US2009/038469, mailed on Sep. 28, 2010, 1 page.
International Search Report and Written opinion for Application No. PCT/US08/061180, mailed on Sep. 5, 2008, 10 pages.
International Search Report and Written opinion for Application No. PCT/US09/038469, mailed on Aug. 10, 2009, 12 pages.
International Search Report and Written Opinion for Application No. PCT/US2011/026193, mailed on Jun. 7, 2011, 17 pages.
International Search Report for Application No. PCT/US09/034555, mailed on May 18, 2009, 5 pages.
International Search Report for Application No. PCT/US2010/061017, mailed on Jun. 16, 2011, 7 pages.
International Search Report for Application No. PCT/US2010/061042, mailed on Mar. 31, 2011, 3 pages.
International Search Report for Application No. PCT/US2010/061081, mailed on Jun. 6, 2011, 7 pages.
International Search Report for Application No. PCT/US2011/043119, mailed on Feb. 15, 2012, 6 pages.
Kim J.H., et al., "The Analysis of Predicted Capsular Bag Diameter using Modified Model of Capsule Measuring Ring in Asians," Clinical and Experimental Ophthalmology, 2008, vol. 36 (3), pp. 238-244.
Liou H.L., et al., "The Prediction of Spherical Aberration with Schematic Eyes," Ophthalmic and Physiological Optics, 1996, vol, 16 (4), pp. 348-354.
Marinho A., "Results are Encouraging for Phakic IOLs, but More Work is needed," Refractive Surgery, 2000, p. 12, 15.
Menapace R., "The Capsular Tension Rings," Journal of Cataract & Refractive Surgery, 2008, Chap. 3, pp. 27-44.
Navarro R., et al., "Accommodation-Dependent Model of the Human Eye with Aspherics," Journal of the Optical Society of America, 1985, vol. 2 (8), pp. 1273-1281.
Olsen T., "Simple Method to Calculate the Surgically Induced Refractive Change," Journal of Cataract & Refractive Surgery, 1993, vol. 19 (2), pp. 319-320.
Praeger D.L., "Praeger Technique for the Insertion of the Copeland Radial IOL Posterior Chamber Placement," Copeland Lens, 1982, 7 pages.
Strenn K., et al., "Capsular bag Shrinkage after Implantation of an Open-Loop Silicone Lens and a Poly(methyl methacrylate) Capsule Tension Ring," Journal of Cataract and Refractive Surgery, 1997, vol. 23 (10), pp. 1543-1547.
Tehrani M., et al., "Capsule Measuring Ring to Predict Capsular Bag Diameter and Follow its Course after Foldable Intraocular Lens Implantation," Journal of Cataract Refractive Surgery, 2003, vol. 29 (11), pp. 2127-2134.
Vass C., et al., "Prediction of Pseudophakic Capsular bag Diameter based on Biometric Variables," Journal of Cataract and Refractive Surgery, 1999, vol. 25 (10), pp. 1376-1381.
WO0154569 Machine Translation, Manfred Tetz and Stephan Schruender, May 12, 2000.

* cited by examiner

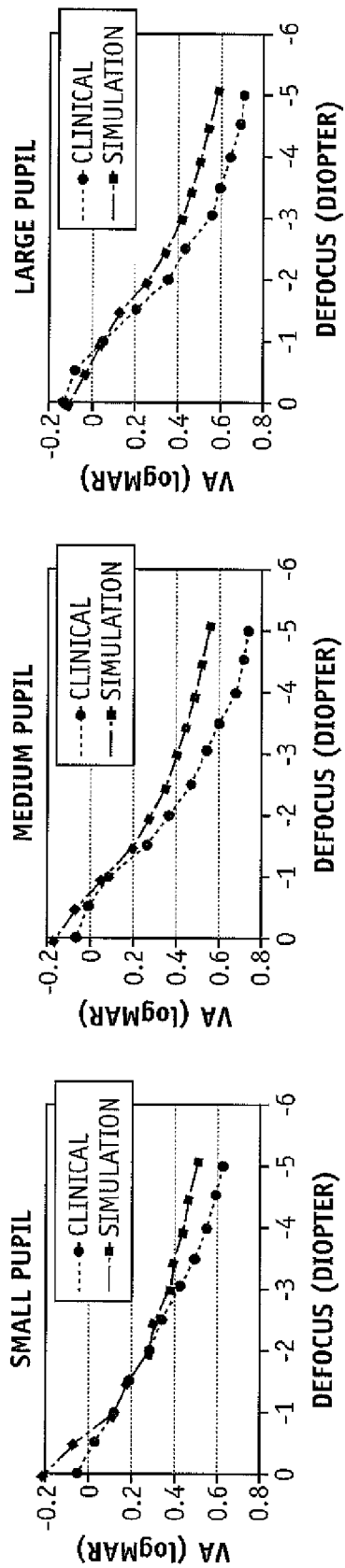
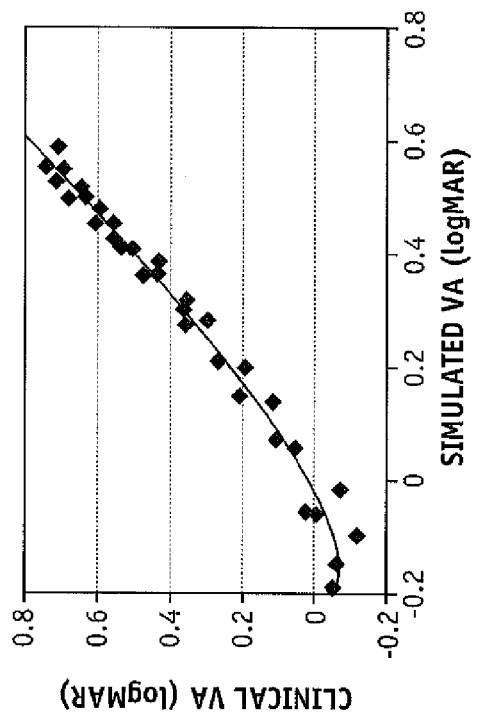
FIG. 9
FIG. 10

APPARATUS, SYSTEM AND METHOD FOR PREDICTIVE MODELING TO DESIGN, EVALUATE AND OPTIMIZE OPHTHALMIC LENSES

CROSS-REFERENCE TO RELATED APPLICATION

N/A

BACKGROUND OF THE INVENTION

1. Field of the Invention

The present invention is directed to lens design and, more particularly, to an apparatus, system and method for predictive modeling to design, evaluate and optimize ophthalmic lenses.

2. Description of the Background

Visual acuity is the clarity of vision, and more specifically is the spatial resolving power of a visual system. Visual acuity is thus the spatial level of detail that can be resolved by the visual system, and may be limited by physiological factors of the patient, such as optical factors within the eye and/or neural factors. Typically, visual acuity is heuristically obtained in an ophthalmic medical practice by presentation of a letter chart to the patient. Visual acuity may be calculated in accordance with the spatial frequency at which the eye's modulation transfer function (MTF) intersects with its neural threshold function (NTF).

The optical transfer function (OTF) describes the spatial variation in a optical system as a function of spatial frequency. The OTF may account for aberration in the optical system, and has a magnitude of the MTF and a phase defined by the phase transfer function (PTF).

An ophthalmic lens may be used to correct aberrations of the eye, as defined using the OTF, for example. An ophthalmic lens may be, for example, an intraocular lens (IOL) that may be surgically implanted, such as a spheric, aspheric, diffractive, refractive, accommodating or injectable IOL, an optical inlay or overlay, or contact lenses or glasses, for example. An IOL is typically implanted to correct medical conditions, such as cataracts and/or presbyopia, for example.

On an individual basis, the modeling of the visual acuity (VA) of ophthalmic lenses using the intersection of the MTF and the NTF has not proven highly accurate when compared with clinical data. Alternative methods of preclinically testing ophthalmic lenses, such as wavefront aberration techniques, have similarly not comported well with clinical data. Further, MTF, wavefront aberration, and other modeling tests have been generally applied to only specific vision conditions, and hence offer only limited predictability of VA and other vision factors, such as contrast sensitivity.

Forty-six (46) physiological eye models for a population of eyes of particular conditions and having particular characteristics have recently been produced by Piers, et al. (See P. A. Piers, H. A. Weeber, P. Artal, and S. Norrby, "Theoretical comparison of aberration correcting customized and aspheric intraocular lenses," J Refract Surg 23(4), 374-384 (2007), incorporated herein by reference as if set forth in the entirety). The Piers models provide clinically-based models of the eye, and encompass a representative model of the clinical population. The representative models include the aberrations that may be presented in the eye, which may additionally indicate the characteristics of the eye, such as the optical length of the eye, the corneal curvature, the pupil size, and variations thereof, for example. More specifically, the Piers eye models demonstrate wavefront aberrations that are characteristic for a cataract population, and which have been verified against clinical data for contrast vision.

Although modeling techniques are available, as discussed above, and although the Piers models provide simulated eyes to which modeling techniques may be applied, modeling techniques have not been applied to model eyes in a manner that allows for the evaluation and optimization of clinical implementations of lenses designed using the modeling. More particularly, the available art fails to provide feedback from clinical implementations to evaluate and optimize lens design, and to thereby improve the obtained characteristics of subsequent clinical implementations.

Thus, the need exists for an apparatus, system and method for predictive modeling to design, evaluate and optimize ophthalmic lenses.

SUMMARY OF THE INVENTION

The present invention is and includes an apparatus, system and method for predictive modeling to design, evaluate and optimize ophthalmic lenses. Ophthalmic lenses may include, for example, contacts, glasses or intraocular lenses (IOLs).

A system for designing, optimizing and evaluating a clinical implementation of an ophthalmic lens may include a plurality of eye models associated with at least one processor, wherein ones of the eye models are indicative of at least one condition of an eye, and a simulator instantiated by the at least one processor that models the ophthalmic lens in at least one of the eye models. The simulator may output at least one simulated outcome, including at least first characteristics of the eye models into which is placed the ophthalmic lens. The system may further include at least one clinical input to the at least one processor, wherein the clinical input includes at least an outcome indicative of the clinical implementation of the ophthalmic lens, and a comparator instantiated by the at least one processor that compares at least the simulated outcome and the clinical outcome, and that compares the differences between the simulated outcome and the clinical outcome to a predetermined tolerance threshold. The at least one processor may optimize the one of the eye models and/or the simulator in order to bring the differences within the predetermined tolerance threshold.

In accordance with the present invention, the outcomes in the exemplary system, method and apparatus may include, for example, performance criteria of the eye, such as visual acuity and contrast sensitivity, for example. The predetermined tolerance threshold may preferably relate to these performance criteria of the eye, for example. Similarly, the conditions may include viewing conditions, such as object distance, light level, off-axis vision, object contrast, visual task, and the like. The characteristics of the eye may include pupil size, off-axis vision, corneal optical power, optical aberrations, such as chromatic and spherical aberration, astigmatism, coma, trefoil, and residual accommodation, for example. Characteristics may also be or be derived from patient group characterizations, such as post-Lasik patients, myopes, patients with neural or retinal conditions, any of which characterizations may be may be delineated by gender, age and race, for example.

An exemplary system may further include, for example, the clinical input from a local input, and/or the clinical input from a remote input, such as a remote input conveyed across at least one network. Correspondingly, the network aspects of the present invention may allow for provision of a computerized graphical user interface embodying the aspects of the present invention.

A method of optimizing, evaluating or designing an ophthalmic lens may include receiving a first lens design for the ophthalmic lens, simulating, for example, the performance provided by the first lens design in at least one modeled eye having a plurality of first characteristics, and receiving clinical performance of the first lens design in at least one patient eye having the plurality of first characteristics. The exemplary method may further include comparing the clinical performance and the simulated performance, and optimizing the first lens design to a second lens design in accordance with the comparing. The optimizing may include, for example, at least modifying the simulating step.

The first and second lens designs may have associated therewith, for example, a parameter, such as a visual acuity and/or a contrast sensitivity, that may provide the basis for the comparing and optimizing steps. The characteristics may include performance characteristics, and/or conditions, topologies, or aspects of the eye, for example. Further, the comparing step and/or the optimizing step of the exemplary method may include weighting of, for example, ones of the characteristics, and/or of the simulated or clinical performance.

An exemplary apparatus in accordance with the present invention may include a design tool for designing a lens for implantation in an eye having a plurality of characteristics, a simulator for simulating performance of the lens in at least one modeled eye having the plurality of characteristics, at least one input for receiving clinical performance of the lens in the eye having the plurality of characteristics, a comparator for comparing outcomes of the clinical performance and the simulated performance, and an optimizer for optimizing a subsequent one of the outcomes of the clinical performance responsive to modification of the lens in accordance with at least one modification to the simulated performance.

Thus, the present invention provides an apparatus, system and method for predictive modeling to design, evaluate and optimize ophthalmic lenses.

BRIEF DESCRIPTION OF THE DRAWINGS

Understanding of the disclosure will be facilitated by consideration of the following detailed description of the embodiments, taken in conjunction with the accompanying drawings, in which like numerals refer to like parts and in which:

FIG. 9 is a plot of VA versus defocus for a simulated population and a clinical population;

FIG. 10 is a correlation plot for clinical VA versus sVA;

DETAILED DESCRIPTION OF THE INVENTION

Figure 1:
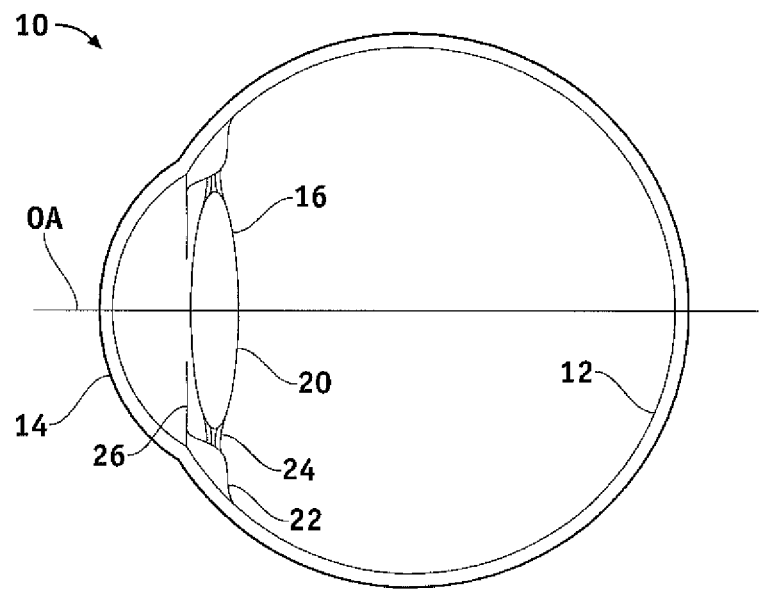
FIG. 1 is an illustration of an eye in the natural state.

It is to be understood that the figures and descriptions of the present invention have been simplified to illustrate elements that are relevant for a clear understanding of the present invention, while eliminating, for the purposes of clarity, many other elements found in typical optical and optical simulation apparatuses, systems and methods. Those of ordinary skill in the art will recognize that other elements are desirable and/or required in order to implement the present invention. However, because such elements are well known in the art, and because they do not facilitate a better understanding of the present invention, a discussion of such elements is not provided herein.

The apparatus, system and method of the present invention may be predictive as to the performance of ophthalmic lenses, such as IOLs, in the eye under any of a variety of circumstances, and with respect to any of a variety of ocular conditions and eye types, and may provide for improved performance of ophthalmic lenses optimized using the modified models indicated by the correspondent clinical results. For example, the present invention may include application of mathematical modeling of certain characterizations of the eye, such as visual acuity (VA) and/or contrast sensitivity, to a series of physiological eye models, such as the 46 physiological eye models provided by Piers, et al., and comparison of model output to actual clinical data, wherein feedback from the actual clinical data may be employed to evaluate and/or modify one or both of the applied mathematical model and the physiological eye model to better approximate one or more indications of the clinical results.

For example, clinical results may be employed in the present invention to determine ones or groups of the 46 model eyes of Piers, such as 1, 10, or all eye models, that optimally model an eye having particular characteristics. Thus, the present invention may provide more accurate model eyes correspondent to clinical eyes having particular characteristics.

It will be appreciated by those of ordinary skill in the pertinent arts that the apparatus, system and method of the present invention may be embodied in one or more computing processors, associated with one or more computing memories, within which is resident computing code to execute the mathematical models discussed herein, to provide the physiological models discussed herein, to track, such as in a relational database, the unique clinical characteristics of the clinical eyes discussed herein, preferably in conjunction with the applied physiological model, and to accumulate feedback regarding the clinical outcome of ophthalmic lenses designed using the system, apparatus and method of the present invention.

Further, those skilled in the art will appreciate, in light of the disclosure herein, that the aspects of the present invention, and most particularly the feedback of the present invention, may be provided to the one or more computing processors for processing via one or more computing networks, including via one or more nodes of a computing network. Computing networks for use in the present invention may include the Internet, an intranet, an extranet, a cellular network, a satellite network, a fiber optic network, or the like. More particularly, the networking aspects of the present invention may allow for provision of the modeling techniques discussed herein to the offices of a myriad of ophthalmic practitioners of one or more selected types, throughout a selected region, throughout a country, or throughout the world, and additionally may allow for the monitoring of clinical test results and the feeding back of those test results from the offices of those practitioners to the apparatus, system and method of the present invention.

FIG. 1 is an illustration of an eye in the natural state. Eye 10 includes retina 12 for receiving an image, produced by cornea 14 and natural lens 16, from light incident upon eye 10. Natural lens 16 is disposed within capsular bag 20, which separates anterior and posterior chambers of eye 10. Iris 26 may operate to change the aperture, i.e. pupil, size of eye 10. More specifically, the diameter of the incoming light beam is controlled by iris 26, which forms the aperture stop of eye 10.

Capsular bag 20 is a resilient material that changes the shape and/or location of natural lens 16 in response to ocular forces produced when ciliary muscles 22 contract and stretch natural lens 16 via zonules 24 disposed about an equatorial region of capsular bag 20. This shape change may flatten natural lens 16, thereby producing a relatively low optical power for providing distant vision in an emmetropic eye. To produce intermediate and/or near vision, ciliary muscles 22 contract, thereby relieving tension on zonules 24. The resiliency of capsular bag 20 thus provides an ocular force to reshape natural lens 16 to modify curvature to provide an optical power suitable for required vision. This change, or "accommodation," is achieved by changing the shape of the crystalline lens. Accommodation, as used herein, includes the making of a change in the focus of the eye for different distances.

Figure 2:
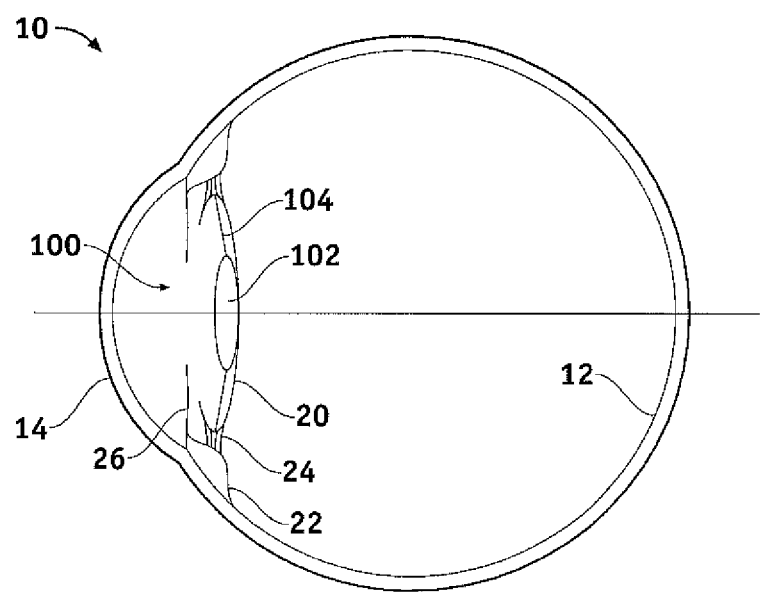
FIG. 2 is an illustration of an eye having an intraocular lens.

FIG. 2, there is shown an eye having natural lens 16 replaced with an IOL 100. Natural lens 16 may require removal due to a refractive lens exchange, or due to a disease such as cataracts, for example. Once removed, natural lens 16 may be replaced by IOL 100 to provide improved vision in eye 10. Eye 10 may include IOL 100 with optic 102, cornea 14, retina 12, and haptics or support structure 104 for centering optic 102. The haptics 104 may center optic 102, and may transfer ocular forces from ciliary muscle 22, zonules 24, and/or capsular bag 20 to optic 102 to change the shape, power, and/or axial location of optic 102 relative to retina 12.

Figure 3A:
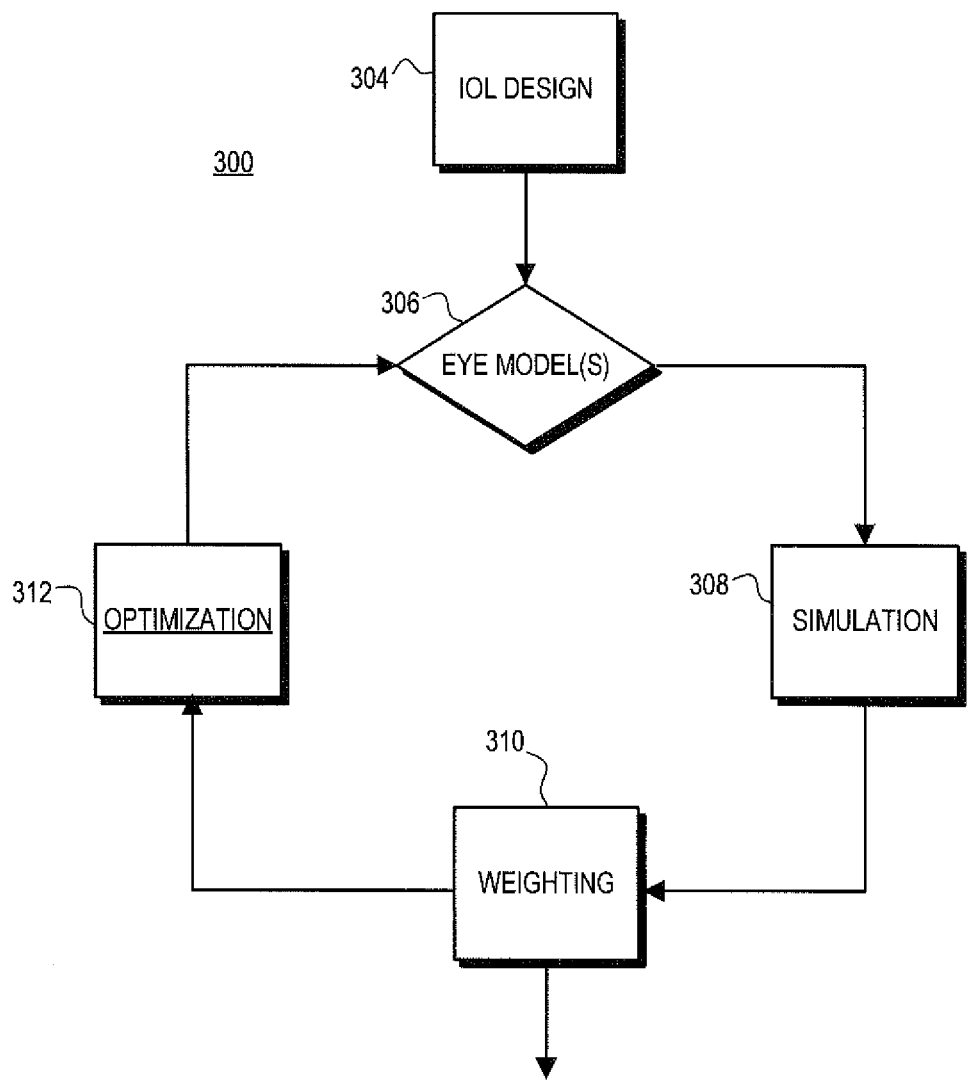
FIGS. 3a, 3b and 3c are flow diagrams illustrating a method for optimizing an ophthalmic lens in accordance with the present invention.

FIG. 3a is a flow diagram illustrating a method 300 of optimizing an ophthalmic lens 100, such as, for example, the IOL illustrated in FIG. 2, in accordance with the present invention. In the illustrated method 300, an ophthalmic lens may be designed and/or provided at step 304 for modeling and for clinical application. Such a lens may, for example, have associated therewith a particular design parameter or parameters. The design parameter or parameters may comprise an optical shape determined by inputting a set of patient parameters into an optimizer. The design parameter or parameters may be derived by the optimizer by determining at least one coefficient of a set of Zernike polynomials. For example, calculating the design parameter or parameters often includes determining a plurality of selected Zernike coefficients, such as for power, astigmatism, or chromatic or spherical aberration, for example, at various orders. The outcome of the eye at a first viewing condition may be measured while viewing at a first viewing distance, and the outcome of the eye at a second viewing condition may be measured while viewing at a second viewing distance which is less than the first distance.

At step 306, the aforementioned eye models, such as a subset of the aforementioned eye models having topologies and/or characteristics of interest, may be subjected to simulated visual acuity (sVA) modeling at step 308 to predict, for example, VA and/or other factors, such as contrast sensitivity. In the aforementioned example, model eyes similar in characteristics to the eye for which the design parameter or parameters are to be obtained may be subjected to step 308. Characteristics of interest may include any one or more of a plurality of patient parameter inputs, such as pupil sizes, off-axis vision, and object distance vision, corneal optical power, or residual accommodation by gender, age or race, for example. Similarly, characteristics may include particular aberrations, and/or aberrations of particular severity, such as astigmatism, presbyopia, and chromatic and spherical aberration, for example.

At step 310, weighted factors to optimize vision and/or performance of lens 100 may be applied, wherein the factors may include, for example, clinical performance of the lens 100 as designed at step 304. Weight factors may be assigned, for example, to each of the characteristics and/or topologies discussed above. For example, the parameters of an ophthalmic lens may be determined, at least in part, by iteratively optimizing a threshold tolerance, such as by optimizing a patient's VA obtained with the corrective parameters, wherein the patients have a clinical eye characterized similarly to the characteristic eye model or models selected.

The lens 100 may be evaluated, adjusted and/or optimized at step 312, such as a clinical adjustment to the designed lens for actual implantation, or such as a modification to the model of the designed lens for feedback to step 306. For example, the parameters may be optimized for a characteristic eye by scaling a refractive shape, and/or by analytically or numerically deriving an optical shape providing the desired optical powers at an associated plurality of viewing conditions. The modification to the lens design for modeling may be made pursuant to failure of the lens design to meet a predetermined threshold tolerance in clinical implementation, and may include verification of the current lens design or recommendation of an alternative lens altogether.

Figure 3B:
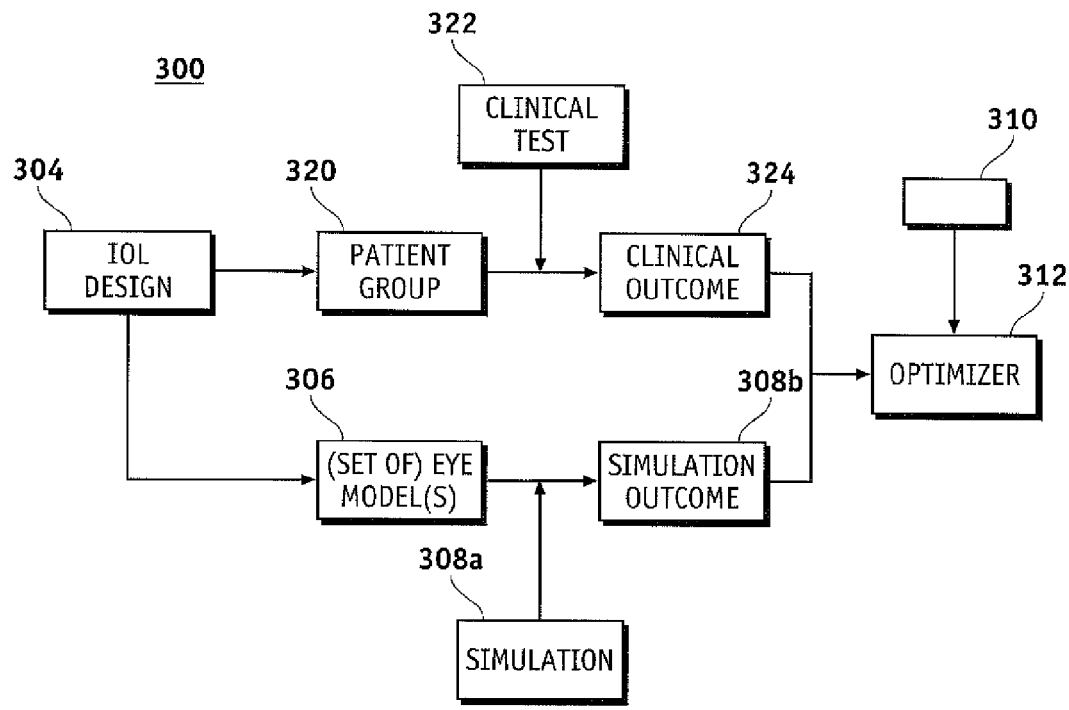

FIG. 3b is a more detailed illustration of the method 300 of FIG. 3a. As illustrated in FIG. 3b, an IOL design may be provided, based on, for example, a design estimation or a design software simulation for particular input conditions, at step 304. At step 306, ones of a plurality of available eye models, preferably in accordance with the particular input conditions used in step 304, are selected. A simulation may be provided, into which are incorporated the lens design from step 304 and the eye models from step 306, at step 308a, which may generate a simulation outcome at step 308b. A patient group for obtaining clinical outcomes may be obtained at step 320, into which are incorporated the lens design from step 304, and to which patient group clinical testing may be applied at step 322. The clinical testing provides clinical outcomes at step 324. Optimization of the lens design at step 304 or the simulation at step 306 may be provided at the optimization step 312, which step 312 may be performed in accordance with a weighting of input conditions and/or simulation outcomes at step 310 (shown in FIG. 3a). For example, at step 310 pupil size may be weighted 2 to 1 over spherical aberration, or VA may be weighted 2 to 1 over contrast sensitivity, in obtaining a desired optimization at step 312.

Figure 3C:
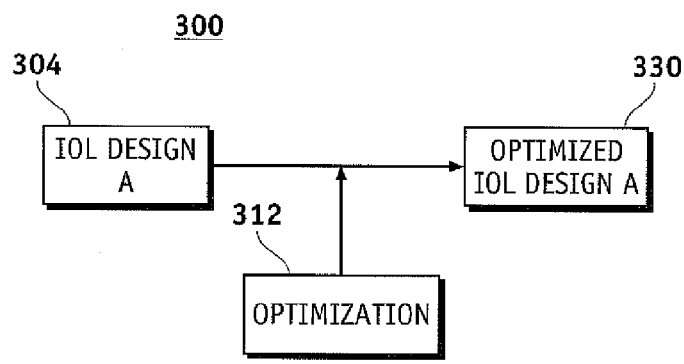

Further, and as illustrated by way of example with respect to FIG. 3c, the method 300 of FIGS. 3a and 3b may be iteratively provided in order to arrive at an improved lens design at step 330. More specifically, a lens may be provided at step 304, and an optimization may be iteratively provided at step 312, with or without the clinical outcome input at step 324, to generate an improved lens design at step 330. Of course, the iteration of step 312 may be performed without clinical outcome input in the event of pre-clinical design, but may preferably include clinical outcome input in order to optimize the simulation for improved clinical lens design output at step 330. Further, the iteration of step 312 may lead to a new or alternative lens design, a modification to an original lens design, or a modification to simulation at step 306, for example.

The threshold tolerance of the present invention is predetermined, and may be predetermined based on literature in the art, based on experience of a patient or group of patients, or from a back-calculation from obtained clinical data, for example. For example, the threshold function may reflect optical quality throughout a particular range, and/or may represent patient tolerable parameters. The threshold function may comprise a ratio of an optical parameter of the eye with a diffraction theory parameter. Thus, exemplary tolerance thresholds may include a threshold of at least one parameter selected from the Strehl Ratio (SR), the MTF, the VA, the point spread function (PSF), the encircled energy (EE), the MTF volume or volume under MTF surface (MTFV), the compound modulation transfer function (CMTF), the contrast sensitivity (CS), and/or dysphotopsia, at any or all predefined viewing conditions. Similarly, the threshold tolerance may also be based on geometrical optics and/or ray tracing. Preferably, minimization or maximization of the threshold tolerance should yield a predictable optimized optical quality of the eye. For example, the threshold tolerance may be a function with a certain number of free parameters to be optimized, via minimization or maximization, through the optimization feedback discussed herein.

More specifically, the threshold tolerance for optimization may be a function of the MTF. As referenced above, MTF may be used to predict visual performance, in part because the MTF at one spatial frequency corresponds to one angular extent of targets. The modulation transfer function (MTF) may be calculated using the formula:

$$MTF(u,v)=FT[PSF(x,y)]\ MTF(u,v)=Re[GPF(x,y)GPF(x,y)]$$

where u and v represent spatial frequencies, Re represents the real part of a complex number, FT represents a Fourier Transform, GPF represents a generalized pupil function, and x and y represent position or field of view.

For example, in a particular exemplary embodiment, the visual acuity in the presence of defocus of a population of cataract patients implanted with diffractive multifocal intraocular lenses may be optimized using method 300. At step 306, method 300 may use the aforementioned set of cataract patient physiological eye models, and/or may use a subset of the physiological eye models having particular eye characteristics and/or topologies, such as a subset of eye models or single eye models that include particular chromatic and higher order aberrations, for example.

The set or subset of the eye models may then be subjected to a simulation, such as a simulated VA modeling, at step 308, and the results compared with clinical outcomes at step 310. Optimization based on the clinical outcome comparisons may be obtained using standard optimization routines, such as the downhill simplex method or the direction set method. The downhill simplex method, for example, starts with an initialization of N+1 points or vertices to construct a simplex for an N-dimensional search, and iteratively endeavors to reflect, stretch, or shrink the simplex by geometrical transformation so that a close-to-global minimum or pre-defined accuracy is found. A more detailed discussion of optimization in an optical system using the downhill simplex and direction set method may be found in U.S. Pat. No. 7,475,986, entitled "Presbyopia Correction Using Patient Data", issued Jan. 19, 2010 and having inventors Dai, et. al, the entire disclosure of which is incorporated herein by reference as if set forth in the entirety.

Simulated VA (sVA) may be determined by first calculating the MTF for each eye model at varying levels of defocus. The sVA is then calculated from the spatial frequency at which the MTF intersects with the neural threshold function (NTF). In this exemplary embodiment, the sVA produced for the eye models may be, for example, systematically 0.05 log MAR units lower (better acuity) than the clinical results, although the difference from the clinical results may be independent of defocus (p=0.98). If either of the simulated versus clinical or the dependence on defocus measures is outside of tolerance threshold, i.e., if the sVA in the eye models differed grossly from the clinical results outside of the predetermined tolerance, and/or if the difference between the modeled and clinical results was highly dependent on defocus, the method 300 may feedback, at step 312, a weighting of the characteristics not within tolerance to indicate an optimization to one or both of the sVA model or the subset of eye models used at step 306.

More particularly, for example, the weighting factors may, as discussed above, be made with respect to the characteristics and/or topologies employed in the selected eye models, and/or may additionally be with respect to the desired clinical outcome. As such, an improved VA may be weighted at 2 to 1 as compared to contrast sensitivity, while a VA may additionally be defined, with respect to field angles, as weighting far vision over near, forward angle over peripheral, and the like, for example.

Method 300 may be similarly employed for more complex lenses, such as for a population of cataract patients implanted with multifocal intraocular lenses (IOLs). Multifocal IOLs may supply two simultaneous focal points, one for distant objects and one for near objects, and may additionally provide a depth of focus that results in improved visual performance at intermediate distances. Such a multifocal IOL is the diffractive Tecnis® Multifocal IOL (model ZM900) by Abbott Medical Optics Inc. Those skilled in the pertinent arts will appreciate, in light of the discussion herein, that other multifocal lenses may be used in the instant invention.

For example, the Tecnis Multifocal IOL design has a diffractive relief pattern on the posterior surface, and splits light in equal amounts to the far and near focus. The diffractive add power for near vision, for example, is +4 diopters. The Tecnis lens additionally provides an aspheric surface on the anterior side of the optic to reduce spherical aberration.

Cataract patients having certain eye characterizations may be bilaterally implanted with the Tecnis lens. For example, only patients with natural pupil diameters between 2.5 and 4.0 mm under photopic lighting conditions may be implanted. Such an eye characteristic may be used to select and/or weight ones of the available models eyes, and or may be weighted against other eye characteristics in the model eyes used, for example.

Several methods may be used to measure the pupil diameter using a pupilometer, such as image analysis techniques and wavefront measurements, including Wavescan RTM (VISX, Incorporated, Santa Clara, Calif.) wavefront measurements, for example. The size of the pupil may at least partially determine the amount of light that enters the eye, and may also have an effect on the quality of the image formed by the light entering the eye. For example, when the pupil is very constricted, a relatively small percentage of the total light falling on the cornea may actually be allowed into the eye. In contrast, when the pupil is more dilated, the light allowed into the eye may correspond to a greater area of the cornea. Of note, accommodation and pupillary constriction work in unison in the healthy eyes when shifting from a far to a near viewing distance, and a fairly linear relation may thus exist between at least a portion of the pupillary constriction and accommodation ranges.

A standardized defocus test may be performed on each implanted patient, such as using a self-calibrating, self-illuminating (85 cd/m$^2$) EDTRS chart placed at 4 meters in front of the patient. Defocus may be introduced by placing successive minus trial lenses in 0.5 D increments over the patient's best distance correction. The relationship between defocus and viewing distance may be determined by: [viewing distance expressed in meters]=1/[defocus expressed in diopters]. Binocular visual acuity at each defocus position may then be measured, and may be from zero (best correction) to −5 diopters at each defocus position, for example. The measured VA at defocus may be used to select or limit the selected eye models in the simulation, and/or may be used to enhance the modeling.

For each individual eye model, the power of the multifocal IOL may be determined, such as based on the eye length and corneal power. A lens may be modeled at a range of 12-25 mm, and preferably 20 mm, in front of the cornea of the modeled eye, and the imaging of the eye models may be traced and refracted for both spherical and cylindrical power. Defocus testing may then be simulated by: placing a point source target at 4 meters in front of the anterior cornea, i.e., at a distance correspondent to that used in the clinical setting; fixing the eye model to a fixed physical pupil diameter of 3.0 mm, corresponding to an average apparent pupil size of approximately 3.3 mm in the clinical setting; varying the power of the spectacle lens in 0.25 diopter increments to obtain defocus; and, at each defocus position, calculating the sVA.

Pursuant to the sVA modeling, differences between the clinical outcomes, on average, and the aforementioned eye models may indicate a need for modification of one or both of the sVA model or the eye models used. Needless to say, the larger the sample size that is fed back through the system to the sVA model and the eye models, the more likely any correction to the modeling will be properly indicative of clinical optimization. As such, the present invention is advantageous in that it may provide a networking among large numbers of practitioners, and thus may accept a large volume of feedback. Further, the feedback provided may be corresponded to the sVA modeling of the eye models used, thus enabling a correspondence, over a large sample size, between sVA modeling of the eye models and clinical outcomes.

Figure 4:
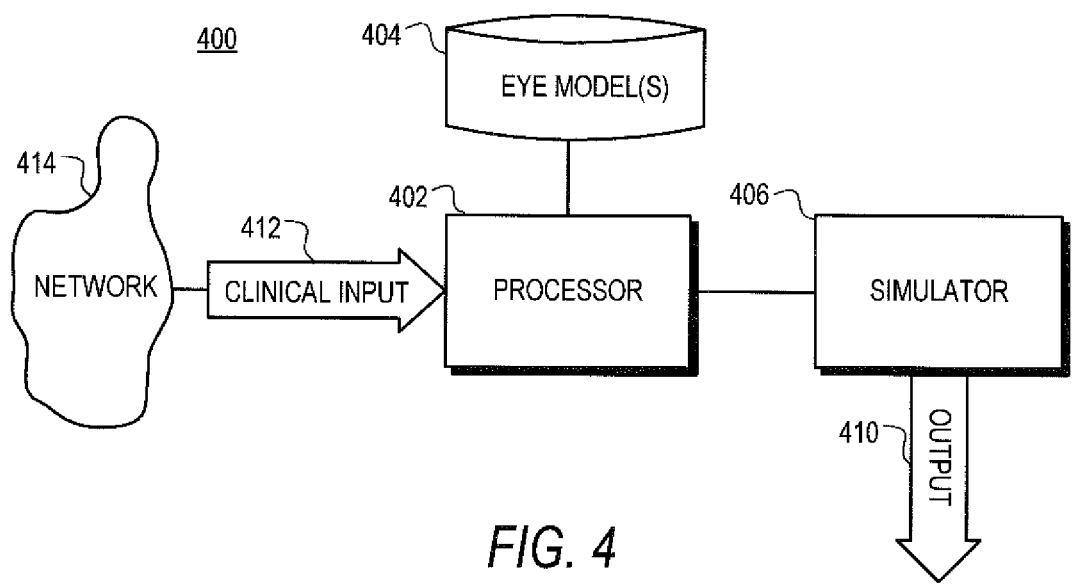
FIG. 4 is a block diagram illustrating a system for optimizing an ophthalmic lens in accordance with the present invention.

FIG. 4 is a block diagram illustrating system 400 in accordance with the present invention. The illustrated system 400 may include at least one processor 402, having associated therewith a plurality of eye models 404, such as the Piers models or subsets thereof, the Liou and Brennan model, the Seidel aberration model, or the Le Grandoye, for patients having particular aberrations, characterizations and/or topologies, and simulator 406. Simulator 406 may be any type of modeling software capable of modeling an ophthalmic lens 100 of a given design in at least one of the eye models 404 provided. Simulator 406 may be embodied as Code V, OSLO, Zemax, ASAP, and similar software modeling programs, for example. The at least one processor 402 applies simulator 406 to at least one eye model 404 to output a simulation 410 of eye characteristics, such as VA and/or contrast sensitivity.

System 400 further includes at least one remote, and may include at least one local, clinical input 412. Clinical input 412 may be provided over at least one network 414, and is input to at least one processor 402 for comparison to the characteristics of simulation output 410. In the event that simulation output 410 is deficient, such as showing suboptimal variance from clinical input 412, processor 402 may act as an optimizer to modify at least one of selected eye models 404, the weights associated with the selected eye models 404 and/or the characteristics of the eye, and the actions of simulator 406, in order to obtain a more suitable simulation output 410 in light of clinical input 412.

As will be understood by those skilled in the pertinent arts, clinical input 412 may, in certain exemplary embodiments, be an average over a predetermined number, or over all, clinical outcomes having one or more predetermined, or all, common topologies and/or characteristics of the patient eye. Correspondingly, eye models 404 used may be a simulated or clinically obtained average over a population having particular characteristics, a simulated or clinically obtained average over a population generally, a simulation matched to a particular patient, a patient type (i.e., cataract patient or LASIK patient), a group of patients, or the like.

More particularly with respect to one of the exemplary embodiments discussed above with respect to FIGS. 3, optimizer may use clinical feedback to design an ophthalmic lens that optimizes patient parameters for patients having certain eye characteristics. For example, the optimizer may optimize the parameters of lenses designed at simulator 406, wherein the simulator initially designed the lens based on patients of a particular pupil diameter and/or having a desired optical power, and wherein optimizer determines variations to the simulation output 410 at simulator 406 based on failure of clinical results to meet the desired optical power tolerance threshold for that parameter(s) in patients having the designed-for pupil diameter.

Moreover, and as referenced above, the method of FIGS. 3 and the system of FIG. 4, and the exemplary embodiments set forth herein, may be implemented using computer hardware and software on a computer readable medium, and the computing hardware and software may preferably be connected to at least one computing network. The software may, for example, be implemented by system 400 to perform method 300, such as via a graphical user interface (GUI) provided in a clinical setting. The GUI may provide any number of graphical panels for convenient use by a clinician, such as three primary panels. The primary panels may include, for example, an optical parameter panel, a clinical outcome input 412 panel, and a recommended action panel that may be based on simulation 410. Needless to say, one or more of the graphical panels may be divided into sub-panels, such as sub-panels for optimizations, verifications, graphs, images, historical data, and the like. The software GUI may also provide menu bars, tool bars, status bars, drop down menus, and the like.

Method 300 and system 400 may be applied to a given population of modeled eyes having predetermined characteristics and/or topologies, such as in order to gain a sufficient sample size to enable optimization of the lens design, the selected eye models, and/or the simulation methodology based on clinical findings. FIGS. 5a-5d are histograms illustrating eye characteristics for a population of model eyes. As illustrated, FIG. 5a shows the corneal power of the eye across a population of model eyes. FIG. 5b shows the description of the topography of a population of model eyes by a 4$^{th}$ order Zernike polynomial. As will be understood to those skilled in the art, Zernike polynomials describe aberrations of the lens from an ideal spherical shape, which aberrations may result in refraction errors.

The histogram of FIG. 5c illustrates the axial length of the eye across a population of model eyes. Finally, FIG. 5d is a histogram of the magnitude of the total refractive errors of the eye across a population of model eyes using root-mean squares (RMS). For example, a minimum root-mean-squares (RMS) error may be used to determine the accommodation during different conditions. For instance, if no aberrations are present, and there is 2 D of residual accommodation, such a patient uses 0.5 D of residual accommodation when visualizing a target at 2 meters. Moreover, the patient uses all 2 D of residual accommodation to view a target at 0.5 meters. However, the patient would have difficulty viewing targets closer than 0.5 meters, as the residual accommodation is exhausted and no longer available.

Figure 5:
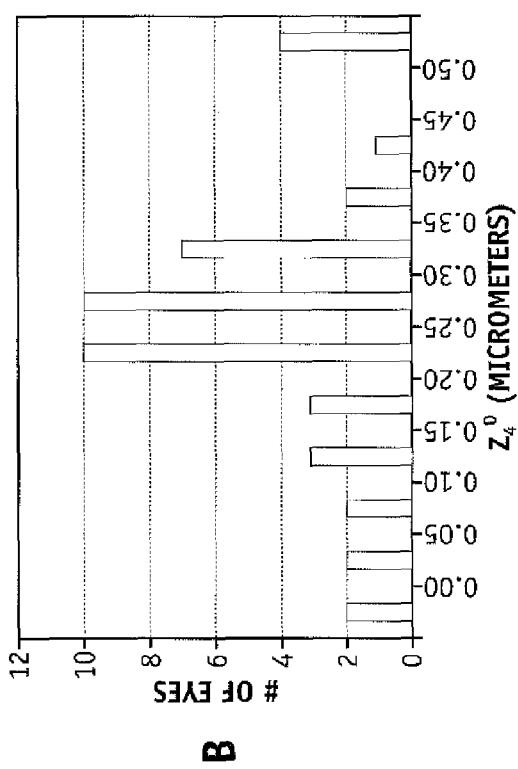
FIGS. 5a-5d are histograms illustrating eye characteristic distributions for model eye populations.
Figure 5:
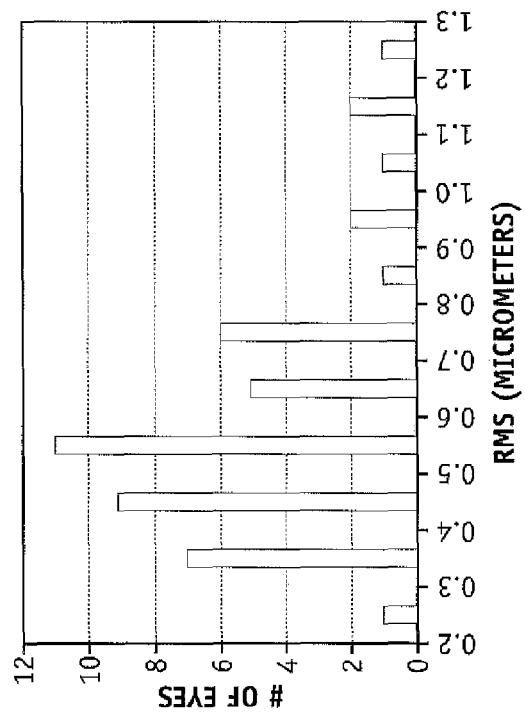
Figure 5:
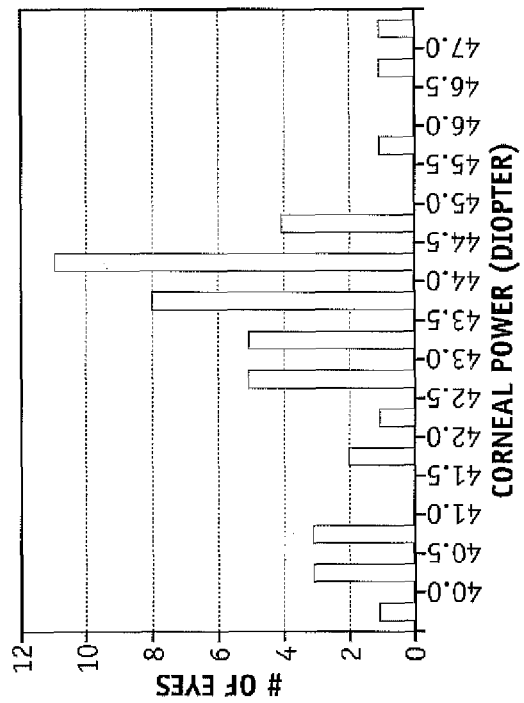
Figure 5:
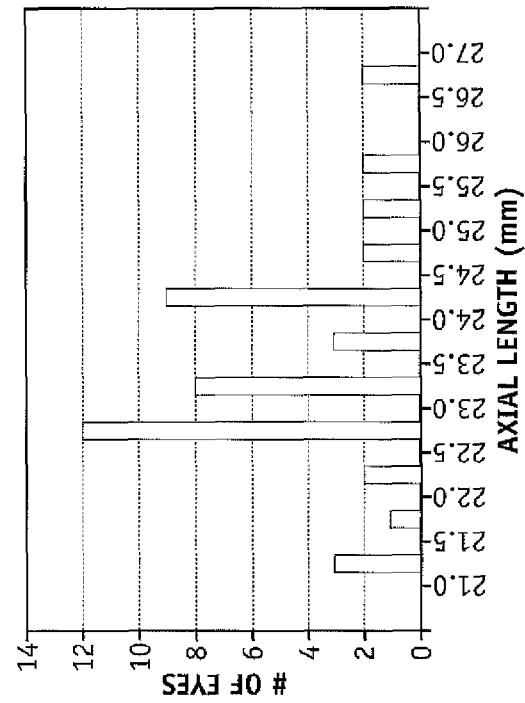
Figure 6:
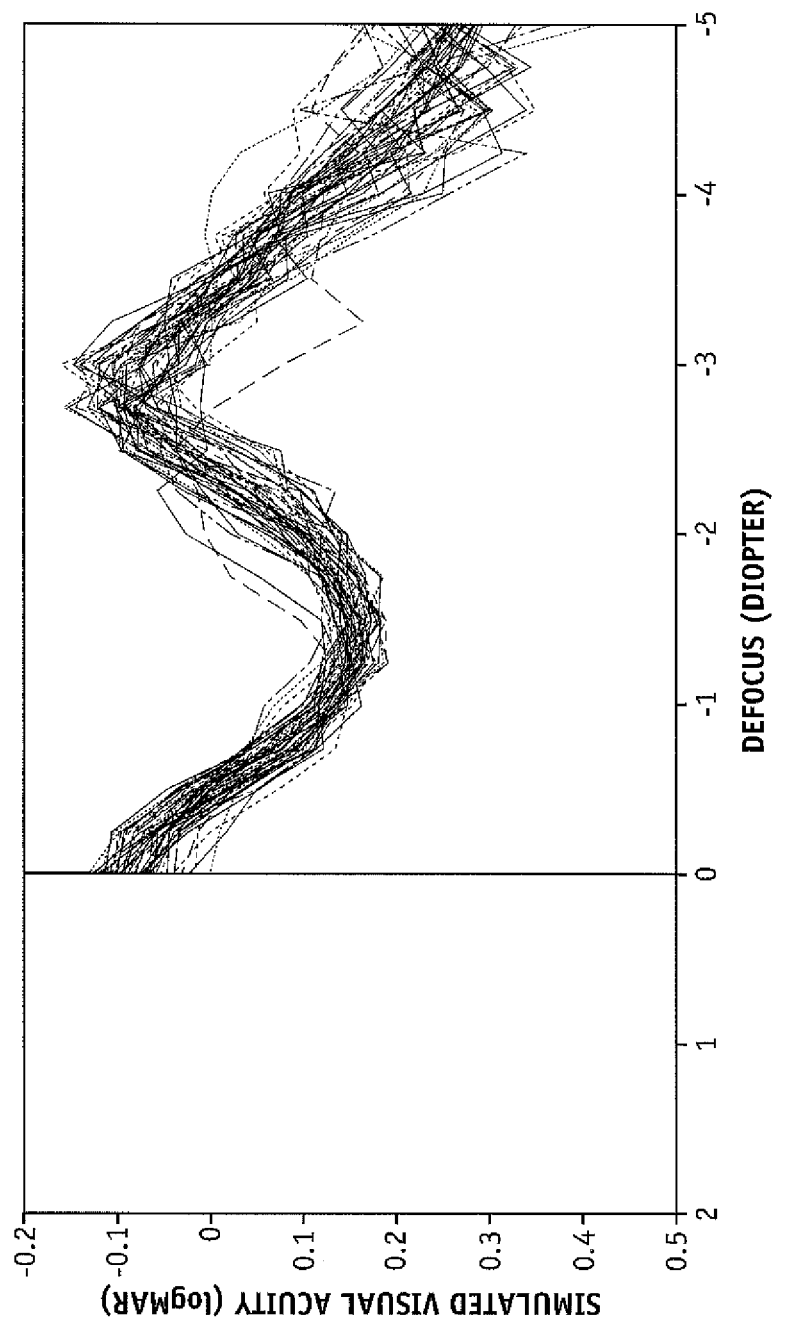
FIG. 6 is a plot illustrating sVA plots across 46 Piers eye models.

While FIGS. 5 illustrates characteristics of populations of eyes within the Piers physiological models, FIG. 6 is a plot illustrating the sVA across the 46 Piers eye models. As shown, the sVA is plotted against defocus, wherein the defocus is varied to simulate performance of the eye. Upon simulation, ones of the eye models having similar characteristics and/or topologies to the clinical eye(s) of interest may be plotted against the clinical eye(s) of interest, such as to obtain a comparative plot of the sVA and clinical performance. Such comparative plots are illustrated in FIGS. 7, and may be used in the method 300, for example, in order to assess optimizing modifications to be made to at step 312 of FIGS. 3.

FIGS. 7a-7c are plots illustrating sVA (light plot) and clinical VA (dark plot) versus defocus, for a population of eyes having varying pupil characteristics. Defocus has is mathematically expressed above. For example, FIG. 7a illustrates a comparison of average clinical VA and sVA for a set of eyes having a small pupil, FIG. 7b illustrates the same comparison for a set of eyes having a medium pupil, and FIG. 7c illustrates the comparison for a set of eyes having a large pupil.

Figure 7:
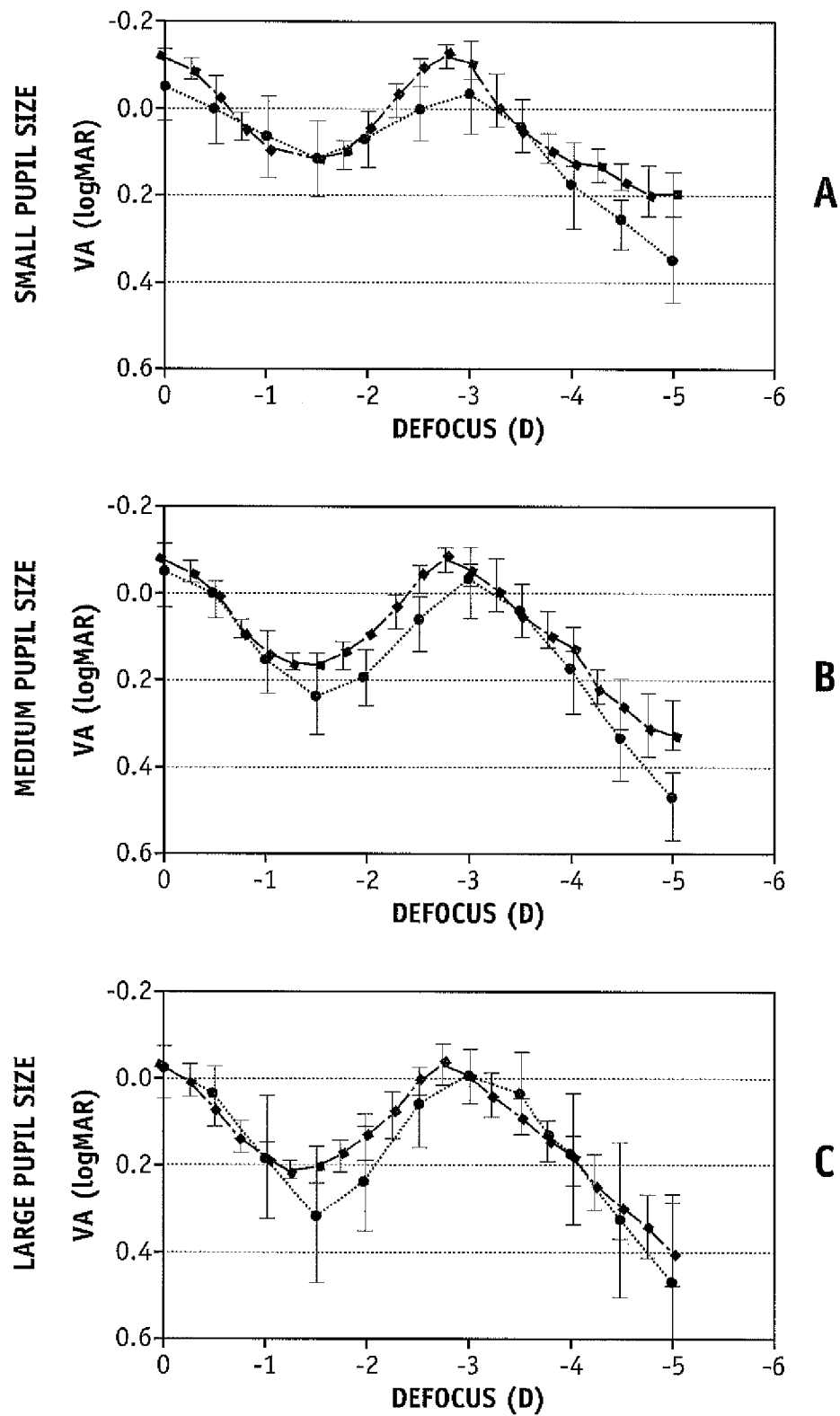
FIGS. 7a-7c are differential plots illustrating clinical VA versus sVA over a range of defocus for different eye characteristics.
Figure 8:
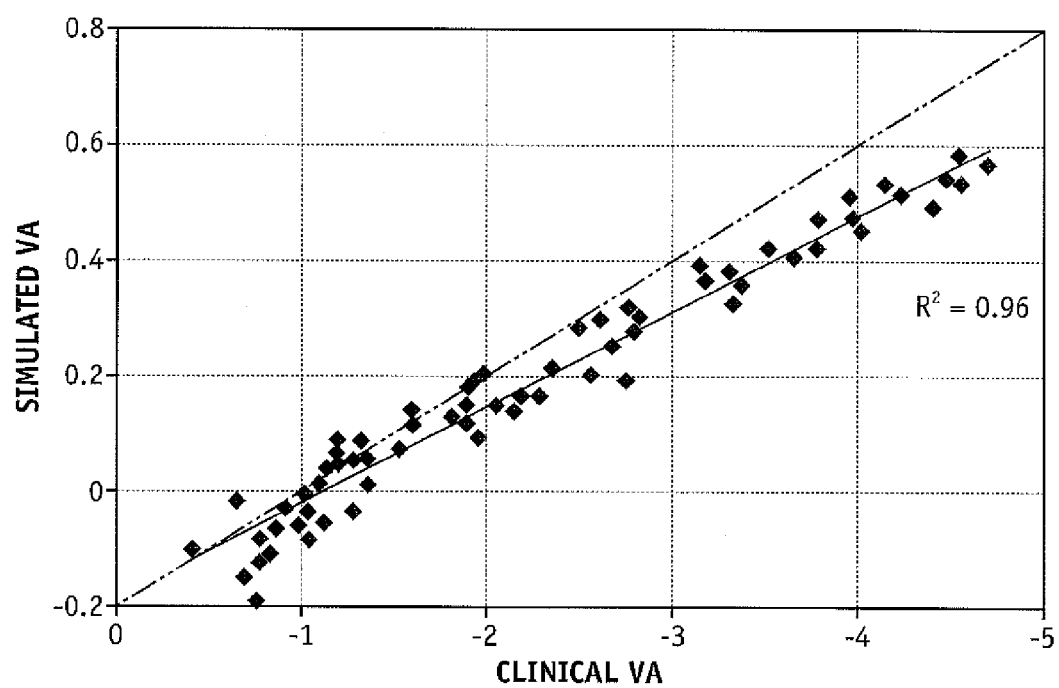
FIG. 8 is a correlation plot for clinical VA versus sVA.

As indicated by the plots of FIGS. 7, clinical VA and sVA for a set of modeled eyes may vary over a range of defocus for different eye characteristics. This variation over the range of defocus may also provide secondary characteristics via the comparison, such as the plot of FIG. 8 showing the correlation between clinical VA and sVA. As discussed above, particularly with respect to FIGS. 3 and 4, the difference between the clinical VA and sVA, and/or the secondary characteristics of the difference, may have an accepted tolerance threshold within which the simulation is deemed to acceptably define the clinical implementation of the lens. More particularly, a designed lens may be modified until the lens is optimized in accordance with the simulation, and that lens, once clinically implemented, may be deemed clinically optimal if the clinical VA is within the predetermined tolerance of the sVA. Conversely, if the clinical VA is not within tolerance of the sVA, the difference in the plots of FIGS. 7, and/or the secondary characteristics of the difference as shown in FIG. 8, may be used in the method of FIGS. 3 and the system of FIG. 4 as feedback to modify the simulation. Modification of the simulation may include, for example and as discussed hereinabove, variation in the simulation and/or calculations, changes in the weighting factors, or the weighting of the factors, to modify the lens design, and/or changes to the selected model eye(s).

By way of specific example, the optimization method 300 and system 400 may be applied to a particular IOL design, such as design model 911A by Abbott Medical Optics Inc., and may subsequently dictate the use of an alternative design, such as a multifocal IOL. In this illustration, the model 911A is clinically tested in three groups of normal cataract patients, having small, medium, and large pupils. The clinical outcome of VA as a function of defocus is illustrated in FIG. 9, wherein each line shown depicts an average outcome for the respective group of patients.

For the sVA, three sets of the 46 Piers eye models, representing a normal cataract population and having essentially the same or similar characteristics (small, medium and large pupil sizes) to the eyes in the clinical groups, are selected. The design of model 911A is modeled for the sVA as a function of defocus, and the results are illustrated in FIG. 9, wherein each line depicts the average outcome for the respective set of eye models.

The differences between the simulation outcome, namely the sVA in this example, and the clinical outcome, namely the VA in this example, are assessed. FIG. 10 illustrates the correlation between the sVA and the clinical VA, wherefrom the differences between the sVA and the clinical VA may be assessed.

Figure 11:
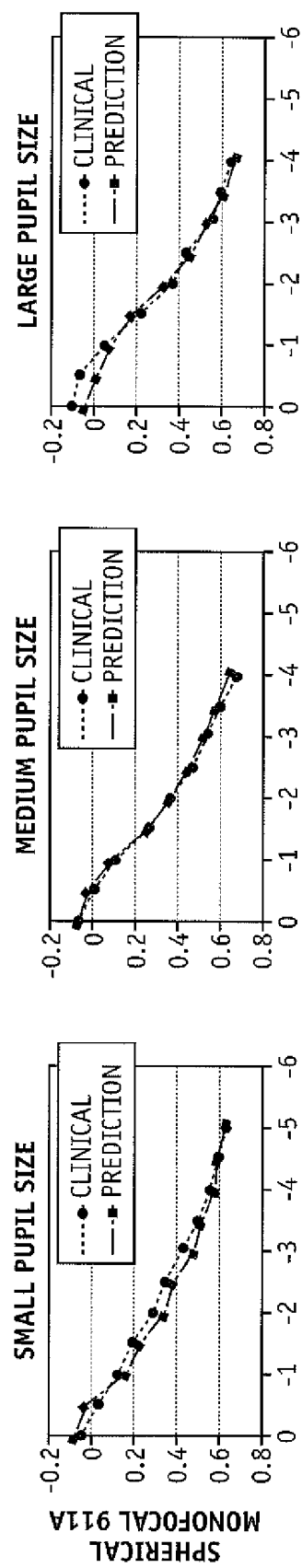
FIG. 11 is an illustration of an outcome for clinical VA versus sVA.
Figure 12:
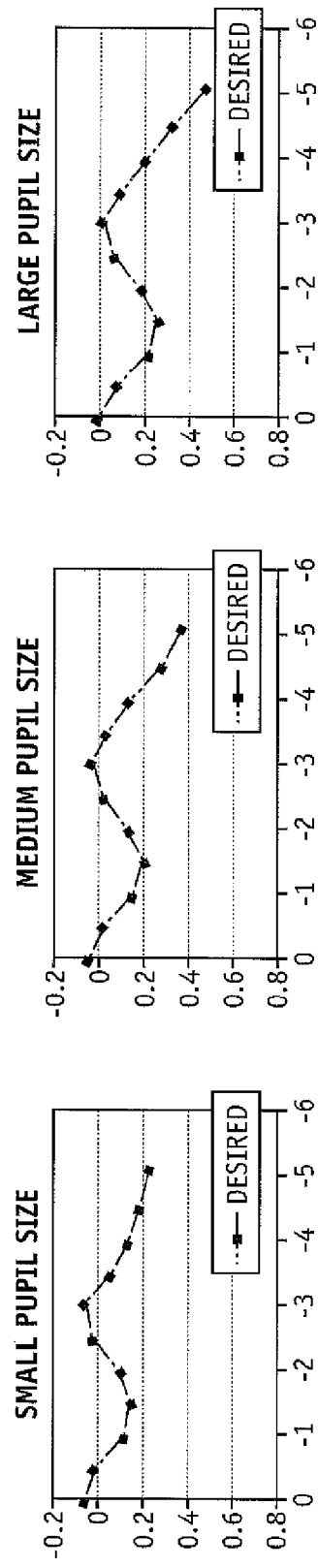
FIG. 12 is an illustration of a desired defocus curve.

FIG. 11 illustrates the optimization of the modeled lens based on the assessed differences, and compares the optimized simulated outcome to the clinical outcome. The optimized simulation may be used to generate a new IOL design to be optimally provided for the same groups of cataract patients. In this exemplary embodiment, a multifocal IOL design may be employed to provide the desired visual acuity shown in FIG. 12.

Figure 13:
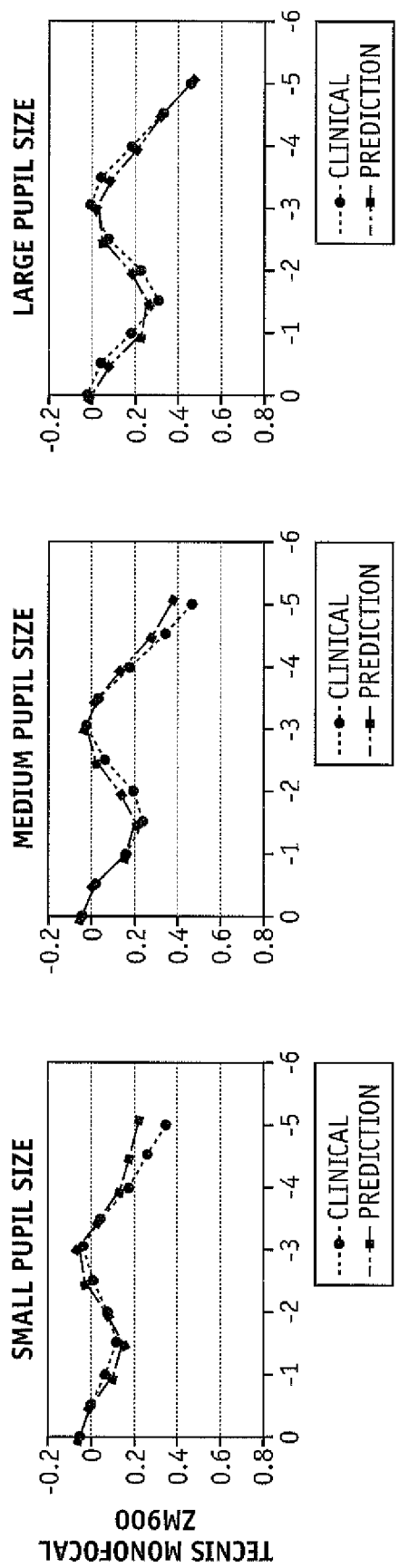
FIG. 13 is an illustration of an outcome for clinical VA versus sVA.

An IOL design that matches the desired outcome, according to the simulation outcome, is the aforementioned Tecnis Multifocal IOL model ZM900. The IOL model ZM900 may thus be implanted in the three groups of normal cataract patients having small, medium, and large pupils. The clinical outcome, expressed as VA as a function of defocus, is illustrated in FIG. 13, wherein each line depicts the average outcome for each group of patients. The differences between the sVA and the clinical VA may again be assessed, and used to iteratively optimize the simulator, or the recommended lens, as desired, for example. In accordance with FIG. 13, those skilled in the art will appreciate that the use of simulation in the present invention resulted in a lens design, namely model ZM900 in this example, that closely matched clinical performance, although the simulation was based on a different lens design, namely model 911 in this example.

Needless to say the illustration immediately hereinabove is provided by way of example only, and may be applicable to lens design, modification of physical lens design, modification to simulation, modification to selections of eye models, and the like. Similarly, the illustration is applicable to not only groups of patients, or with regard to current lens designs, but is equally applicable to custom and quasi-custom lens design, for individual patients and limited or unique subsets of patients, respectively.

Although the invention has been described and pictured in an exemplary form with a certain degree of particularity, it is understood that the present disclosure of the exemplary form has been made by way of example, and that numerous changes in the details of construction and combination and arrangement of parts and steps may be made without departing from the spirit and scope of the invention.

What is claimed is:

1. A system for optimizing a clinical implementation of an ophthalmic lens, wherein the ophthalmic lens is indicated for treating at least one condition of a set of eyes, comprising:
   an eye model associated with at least one processor, wherein the eye model is indicative of residual accommodation, and wherein the at least one condition comprises off-axis vision, post-LASIK patients, and combinations thereof;
   a simulator provided by the at least one processor that models the ophthalmic lens in the eye model having at least a first characteristic, wherein the simulator outputs a first outcome, the first outcome comprising simulated visual acuity at multiple levels of defocus of the ophthalmic lens in the eye model;

at least one clinical input to the at least one processor comprising at least a second characteristic of a clinical eye associated with the clinical implementation, wherein the second characteristic at least substantially overlaps the first characteristic, and a second outcome, the second outcome comprising clinical visual acuity at multiple levels of defocus indicative of the clinical implementation of the ophthalmic lens; and a comparator instantiated by the at least one processor that compares the simulated visual acuity at multiple levels of defocus and the clinical visual acuity at multiple levels of defocus, and then compares differences between the simulated visual acuity at multiple levels of defocus and the clinical visual acuity at multiple levels of defocus to a predetermined tolerance threshold;

wherein the at least one processor modifies the eye model to optimize at least the simulated visual acuity at multiple levels of defocus to bring the differences within the predetermined tolerance threshold.

2. The system of claim 1, wherein the first outcome additionally comprises a simulated contrast sensitivity and the second outcome additionally comprises a clinical contrast sensitivity for at least one predetermined viewing condition, and wherein the comparator additionally compares the simulated contrast sensitivity and the clinical contrast sensitivity, and additionally compares differences between the simulated contrast sensitivity and the clinical contrast sensitivity to a second predetermined tolerance threshold.

3. The system of claim 2, wherein the second predetermined tolerance threshold comprises a comparative level of contrast sensitivity.

4. The system of claim 1, wherein the second outcome additionally comprises a clinical outcome parameter.

5. The system of claim 1, wherein at least one of the at least one clinical input comprises a remote input.

6. The system of claim 5, wherein the remote input is provided over at least one network.

7. The system of claim 1, wherein at least one of the at least one clinical input comprises a local input.

8. The system of claim 1, wherein the predetermined tolerance threshold comprises a comparative level of visual acuity.

9. The system of claim 1, further comprising at least one graphical user interface, wherein the at least one clinical input is provided from, and the optimization is provided to, the at least one graphical user interface.

10. The system of claim 1, wherein the ophthalmic lens comprises an intraocular lens.

11. A method of optimizing a design of an ophthalmic lens, comprising:

receiving a first lens design-for the ophthalmic lens;

simulating, by using an eye model, a simulated visual acuity at multiple levels of defocus provided by the first lens design and residual accommodation; in at least one modeled eye having a plurality of first characteristics, wherein the plurality of first characteristics include at least one of off-axis vision, post-LASIK patients, and combinations thereof;

receiving a clinical visual acuity at multiple levels of defocus of the first lens design in a plurality of patient eyes having a plurality of second characteristics;

comparing the clinical visual acuity at multiple levels of defocus and the simulated visual acuity at multiple levels of defocus; and optimizing, using at least one processor, the first lens design to a second lens design in accordance with the comparing;

wherein the comparing comprises comparing a difference between the clinical visual acuity at multiple levels of defocus and the simulated visual acuity at multiple levels of defocus to a predetermined tolerance threshold.

12. The method of claim 11, wherein the optimizing is responsive to different weightings of one of the plurality of first characteristics.

13. The method of claim 12, wherein the comparing is based on the different weightings.

14. The method of claim 11, wherein the optimizing is responsive to different weightings of the simulated visual acuity at multiple levels of defocus and the clinical visual acuity at multiple levels of defocus.

* * * * *